(12) United States Patent
Griffin

(10) Patent No.: US 8,414,629 B2
(45) Date of Patent: Apr. 9, 2013

(54) LIMITING RADIAL PRELOADS IN SECURING AN ORTHOPEDIC FASTENER

(76) Inventor: T. Hall Griffin, Longview, TX (US)

( * ) Notice: Subject to any disclaimer, the term of this patent is extended or adjusted under 35 U.S.C. 154(b) by 585 days.

(21) Appl. No.: 12/592,235

(22) Filed: Nov. 20, 2009

(65) Prior Publication Data

US 2011/0125197 A1    May 26, 2011

(51) Int. Cl.
*A61B 17/04* (2006.01)
*A61B 17/86* (2006.01)
*A61F 2/08* (2006.01)

(52) U.S. Cl.
USPC .......................................... 606/312; 606/309

(58) Field of Classification Search .................. 606/309, 606/312, 315–317
See application file for complete search history.

(56) References Cited

U.S. PATENT DOCUMENTS

| | | | |
|---|---|---|---|
| 5,242,447 A | | 9/1993 | Borzone |
| 5,593,410 A | | 1/1997 | Vrespa |
| 5,665,087 A | | 9/1997 | Huebner |
| 5,961,524 A | | 10/1999 | Crombie |
| 6,001,101 A | * | 12/1999 | Augagneur et al. .......... 606/316 |
| 6,099,529 A | * | 8/2000 | Gertzman et al. ........... 606/309 |
| 6,375,657 B1 | | 4/2002 | Doubler et al. |
| 6,565,573 B1 | | 5/2003 | Ferrante et al. |
| 6,689,137 B2 | | 2/2004 | Reed |
| 6,743,233 B1 | | 6/2004 | Baldwin et al. |
| 6,949,100 B1 | | 9/2005 | Venturini |
| 6,953,463 B2 | | 10/2005 | West, Jr. |
| 7,001,389 B1 | | 2/2006 | Navarro et al. |
| 7,198,488 B2 | | 4/2007 | Lang et al. |
| 2001/0047175 A1 | | 11/2001 | Doubler et al. |
| 2002/0045897 A1 | | 4/2002 | Dixon et al. |
| 2003/0158555 A1 | | 8/2003 | Sanders et al. |
| 2004/0044345 A1 | | 3/2004 | Demoss et al. |
| 2006/0116686 A1 | | 6/2006 | Crozet |
| 2007/0053765 A1 | | 3/2007 | Warnick et al. |
| 2008/0177335 A1 | | 7/2008 | Melkent |
| 2010/0168802 A1 | | 7/2010 | Pathak |

OTHER PUBLICATIONS

Timothy L. Biliouris et al.: "The effect of radial preload on the implant-bone interface: a cadaveric study"; Journal of Orthopaedic Trauma, vol. 4, No. 3, pp. 323-332; c 1989.
C. Hyldahl et al:"Induction and prevention of pin loosening in external fixation: an in vivo study on sheep tibiae"; Journ. of Orth. Trauma, vol. 5, No. 4, pp. 485-492; c 1991.

(Continued)

*Primary Examiner* — Andrew Yang
*Assistant Examiner* — Olivia C Chang
(74) *Attorney, Agent, or Firm* — Zeman-Mullen & Ford, LLP

(57) ABSTRACT

An orthopedic fastener rated to be received into a corresponding bone specimen. The corresponding bone specimen has (1) an overall outer thickness from near cortex to far cortex in a predetermined rated range of outer bone thicknesses, and (2) a predetermined bone hole preparation including an entry portion in the near cortex. The entry portion has a predetermined minimum entry diameter. The fastener provides a tapered portion. When the fastener is operably secured into the far cortex of a bone thickness for which it is rated to be received, the tapered portion of the fastener contacts the entry portion in the near cortex so as to impart no more than about 0.2 mm of radial preload into the bone surrounding the entry portion.

19 Claims, 4 Drawing Sheets

OTHER PUBLICATIONS

International Search Report and Written Opinion of the International Searching Authority issued in PCT/US2010/056905 and mailed May 30, 2011 and Informal Comments on Written Opinion and International Search Report filed in PCT/US2010/056905 on Aug. 25, 2011.
Author Unknown, "The basics of internal fixation" (8 pages), date circa 2005, downloaded from Internet at http://www.rcsed.ac.uk/fellows/lvanrensburg/classification/commonfiles/basics_of_internal_fixation.htm.
Stratec Medical (aka SYNTHES), "External Distal Radius Fixator, Supplement to the 8 mm rod fixator system: Surgical technique" (11 pages), date circa 2005, downloaded from Internet at http://www.synthes.com/html/uploads/media/036.000.233.pdf.
Orthofix Limited, "Xcaliber bone screws" brochure (2 pages), date Dec. 2002, downloaded from Internet at http://www.orthofix.com/ftp/assets/Product/Product_Files/XCaliber%20bone%20screw/bone_screws1.pdf.

* cited by examiner

LIMITING RADIAL PRELOADS IN SECURING AN ORTHOPEDIC FASTENER

RELATED APPLICATIONS

This application is related to commonly-invented, concurrently-filed U.S. patent application "Engaging Predetermined Radial Preloads in Securing an Orthopedic Fastener", Ser. No. 12/592248, the disclosure of which is incorporated herein by reference.

FIELD OF THE INVENTION

This invention relates generally to orthopedic fasteners, and more specifically, in preferred embodiments, to orthopedic fasteners configured to exert, when secured into cortical bone, no more than a predetermined amount of radial preload in the cortical bone material surrounding the fastener's regions of contact with the bone.

BACKGROUND OF THE INVENTION

A common complication of fracture repair, external fixation (or other orthopedic procedures in which fasteners are inserted into bone) is loosening of the fastener over time at the fastener/bone interface. In their article "The Effect of Radial Preload on the Implant/Bone Interface: A Cadaveric Study", Biliouris et al. suggest several reasons for this loosening, including micro-movement of the bone tissue as axial or bending loads are exerted on the fastener during normal use of the fastened bone by the patient after surgery. As described in some detail in the above-referenced article (hereafter referred to as "Biliouris et al."), such axial and bending loads can cause circumferential and other micro-displacement of the fastener as secured into the bone. This micro-displacement temporarily deforms the shape and size of the bone hole into which the fastener is secured, resulting in loss of circumferential contact between the fastener and the bone, which in turn leads to higher stress conditions at the remaining areas of contact. However, while the higher elasticity of the metal fastener allows the fastener to resume its original shape and relative position within the bone hole after loading, the lower elasticity of the bone surrounding the bone hole leaves the hole potentially damaged after loading. As a result, there is a loss of contact between fastener and the bone during and potentially after loading, resulting in micro-motion between fastener and bone, manifesting itself over time and repetitive loading as loosening of the fastener.

Biliouris et al. also discuss the use of radial preload to counteract loosening of fasteners under repetitive loads in external fixation. The basic concept of radial preload is to "oversize" the diameter of the fastener within the bone hole. In this way, the bone material around the "oversized" portion of the fastener is compressed, tightening the contact between the fastener and the bone material, encouraging intimate and sustained contact during operational loading, and thereby reducing the propensity for loosening.

However, as taught by Biliouris et al., the bone material's comparatively low elasticity limits the amount of radial preload that can be absorbed by the bone material without causing cracking of the bone material around the oversized portion of the fastener. Biliouris et al. observe that a fastener diameter more than about 0.2 mm greater than the receiving bone hole is prone to cause micro-cracking in surrounding cortical bone material.

The reference in this disclosure so far to "bone" deserves further discussion. Orthopedic fasteners are typically designed to fasten either cortical bone or cancellous bone. Cortical bone, typically found on the outside of a bone, is much tougher and harder than cancellous bone, which is typically found on the inside of a bone. Cancellous bone has soft and malleable characteristics, whereas cortical bone is considerably harder. While radial preload is understood to provide advantages in both cortical and cancellous bone, the inventive focus of this disclosure is on the radial preload imparted by fasteners secured in cortical bone.

U.S. Pat. No. 6,949,100 (Venturini) discloses an orthopedic fixation pin with a tapered thread. While Venturini mentions use in the art of radial preload, Venturini's disclosure and invention focuses on thread profile geometry as a way to enhance the fixation pin's grip on bone.

U.S. Pat. No. 5,961,524 (Crombie) discloses an orthopedic fastener with a tapered thread. The fastener is configured to be received into a smooth hole of substantially the same taper as the thread on the fastener. Once secure into the into the hole, the fastener is given a small amount of extra tightening to compress bone material surrounding the threads in order to improve grip of the fastener on the bone. Crombie's disclosure, however, appears to be solving the problem of improving bone-to-fastener contact rather than imparting limited or controlled amounts of radial preload into the bone surrounding the fastener. As a result, no structure to measure or limit radial preload is disclosed.

U.S. Pat. No. 7,198,488 (Lang et al.), U.S. Pat. No. 5,593,410 (Vrespa) and U.S. Pat. No. 6,953,463 (West, Jr.) illustrate fastener thread styles understood to be advantageous in improving fastener grip in either cortical or cancellous bone. These disclosures provide no guidance, however, on imparting limited or controlled amounts of radial preload into the bone surrounding the fastener.

Likewise U.S. Pat. No. 6.565,573 (Ferrante et al.) and U.S. Pat. No. 6,375,657 (Doubler et al.) disclose bone fasteners with generally tapered threads, but the disclosures of these patents provide no guidance on imparting limited or controlled amounts of radial preload into the bone surrounding the fastener.

U.S. Pat. No. 7,001,389 (Navarro et al.) discloses fasteners with various thread configurations, including tapered threads, to assist in securing a plate to bone. As with other prior art discussed above, however, Navarro et al. provide no guidance on imparting limited or controlled amounts of radial preload into the bone surrounding the fastener.

There is therefore a need in the art for an orthopedic fastener specially designed to exert radial preload on the surrounding bone so that the radial preload reduces the likelihood of loosening of the fastener under repetitive loads. The diameter of such a new fastener will advantageously not exceed the diameter of the bone hole by more than about 0.2 mm along the portions where radial preload is being imparted. In this way, the amount of radial preload imparted into the bone will be limited to no more than about 0.2 mm. Such a new fastener may further, or alternatively, advantageously provide structure, in other embodiments, to engage a predetermined amount of radial preload for a particular installation.

SUMMARY OF THE INVENTION

The present invention addresses one or more of the above-described needs identified in the prior art. One aspect of this invention includes an orthopedic fastener rated to be received into a corresponding bone specimen. The corresponding bone specimen has (1) an overall outer thickness from near cortex to far cortex in a predetermined rated range of outer bone thicknesses, and (2) a predetermined bone hole preparation including an entry portion in the near cortex. The entry portion has a predetermined minimum entry diameter.

The fastener itself comprises a shank providing adjacent threaded and unthreaded portions. The unthreaded portion provides a tapered diameter portion, the tapered diameter portion transitioning from a large taper diameter to a small taper diameter. The small taper diameter is located proximate to the threaded portion, while the large taper diameter is located distal from the threaded portion.

The small taper diameter is not greater than the predetermined minimum entry diameter in the bone hole preparation into which the fastener is rated to be received. The large taper diameter not greater than about 0.2 mm more than said predetermined minimum entry diameter. The tapered diameter portion is located on the shank such that, when the threaded portion on the fastener is secured into the far cortex on a bone specimen having an outer bone thickness in the predetermined rated range, the tapered diameter portion of the fastener contacts the entry portion in the near cortex.

It will be appreciated from the above summary that fasteners of the present invention are rated for particular predetermined bone specimens into which they are to be received and secured. This "rating" aspect of the fasteners is discussed in more detail near the end of the "Detailed Description" section of this disclosure.

It is therefore a technical advantage of the invention to provide an orthopedic fastener that, once secured in a specimen of bone, is less prone to loosening. Assuming that the fastener of the present invention is secured into a bone specimen for which the fastener is rated, the tapered diameter portion on the shank will reside in entry portion in the near cortex when the threaded portion on the fastener is secured into the far cortex.

Now resident in the entry portion, the tapered portion effectively provides an "oversized" portion of the shank operative in the entry portion, in that the tapered diameter portion provides a large taper diameter that is not more than about 0.2 mm greater than the predetermined minimum entry diameter in the entry portion. By being greater than the minimum entry diameter in the entry portion, the large taper diameter therefore exerts radial preload in the entry portion. However, by capping the large taper diameter at about 0.2 mm greater than the minimum entry diameter in the entry portion, the maximum amount of radial preload that can actually be exerted is limited to about 0.2 mm, an amount recognized in the art to be unlikely to cause damage to the cortical bone material surrounding the entry portion. In this way, radial preloads up to about 0.2 mm can be exerted in order to control micro-motion, subject to a limit of about 0.2 mm in order to avoid bone damage.

A further technical advantage of the invention is to provide fasteners that are relatively simple to manufacture, and that can be rated to be received into a variety of bone hole preparations in a variety of bone specimen types and thicknesses.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should be also be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION

Figure 1A:
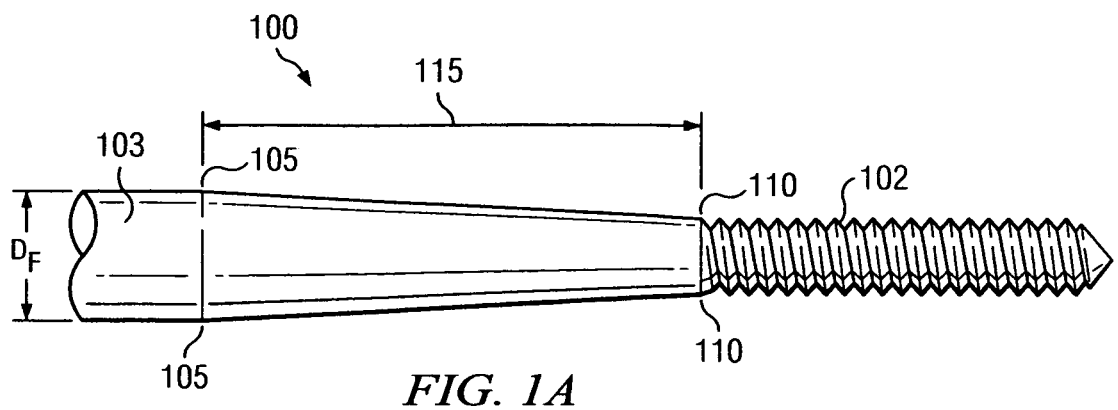
FIGS. 1A, 1B and 1C illustrate, according to a first aspect of the present disclosure, a deployment of fastener 100 into bone specimen 120 through opening 135.
Figure 1B:
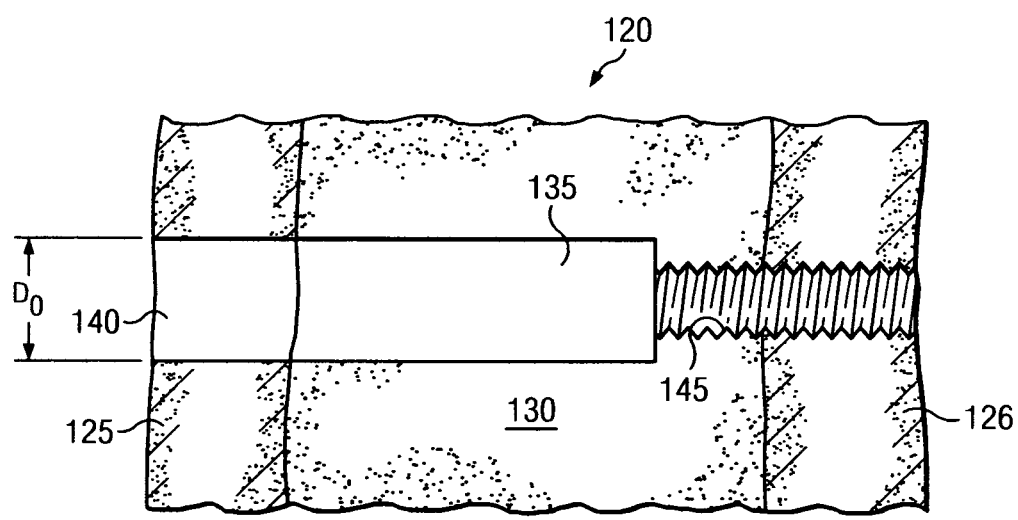
Figure 1C:
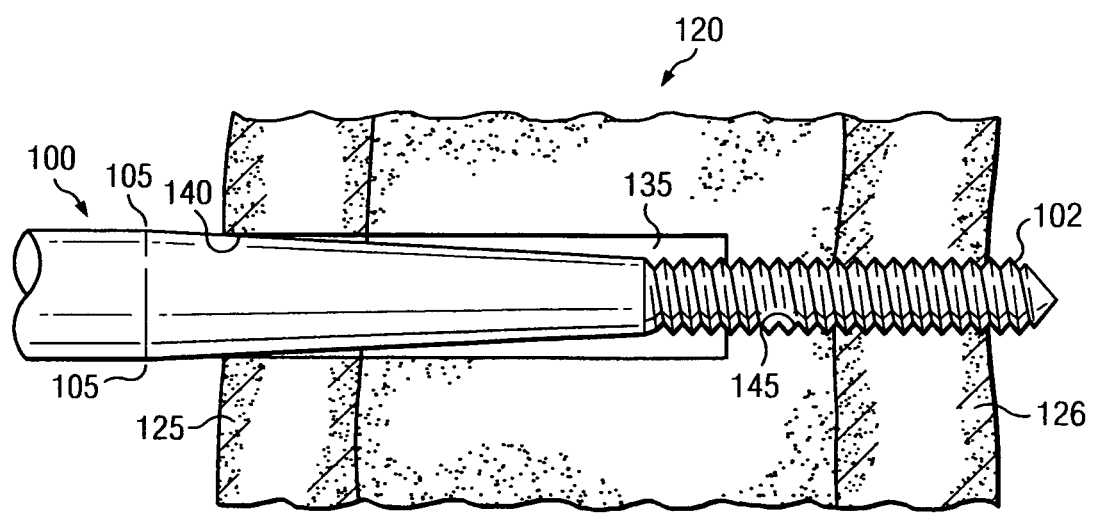

FIGS. 1A, 1B and 1C should be viewed together, and depict a first aspect of the present disclosure, in which an orthopedic fastener 100 is configured to limit and/or control radial preloads exerted in near cortex 125 as fastener 100 is operably secured into bone specimen 120. FIG. 1A illustrates a segment of fastener 100 in isolation. FIG. 1B illustrates bone specimen 120 with opening 135 prepared to receive fastener 100. FIG. 1C illustrates fastener 100 received into opening 135 and operably secured into bone specimen 120.

Referring first to FIG. 1A, fastener 100 provides threaded portion 102 on one end. Fastener 100 further provides unthreaded cylindrical portion 103 with a pre-selected constant diameter $D_F$. Threaded portion 102 and cylindrical portion 103 are separated by a smooth tapered portion 115. Tapered portion 115 is bounded by reference points 105 and 110, as illustrated on FIG. 1A. Reference point 105 is the point at which cylindrical portion 103 ends and tapered portion 115 begins. Reference point 110 is the point at which tapered portion 115 ends. Tapered portion 115 reduces the diameter of fastener 100 from $D_F$, at reference point 105, to a diameter less than $D_F$ at reference point 110. It will be further appreciated that, as described in more detail below with respect to FIG. 1C, the distance on fastener 100 between reference points 105 and 110 is pre-selected.

In the embodiment of fastener 100 depicted in FIG. 1A, threaded portion 102 begins at reference point 110. The invention is not limited in this regard, however. It will be appreciated that in other embodiments (not illustrated), an unthreaded portion may be provided between reference point 110 and threaded portion 102.

Turning now to FIG. 1B, bone specimen 120 is illustrated in cross-section, showing near and far cortices 125, 126 surrounding interior portion 130. It will be appreciated that interior portion 130 may comprise cancellous bone and/or fatty bone marrow. Bone specimen 120 as illustrated on FIG. 1B has been prepared to receive fastener 100 from FIG. 1A. More specifically, opening 135 has been pre-configured to receive fastener 100. Circular entry hole 140 has pre-selected diameter $D_O$, and extends through near cortex 125 into interior portion 130 of bone specimen 120. In the embodiment illustrated in FIG. 1B, opening 135 further provides female threaded section 145 provided through to far cortex 126. The threads on female threaded section 145 are pre-selected to mate with threaded portion 102 on fastener 100 (as shown on FIG. 1A). It will be appreciated that, although not illustrated on FIG. 1B, alternative embodiments will omit female threaded section 145, or provide a small diameter pilot hole in its place suitable to receive self-tapping threads deployed on threaded portion 102. In such alternative embodiments, threaded portion 102 on fastener 100 (as shown on FIG. 1A) will provide self-tapping threads. The inventive material disclosed herein is independent of the manufacturing technique used to provide female threaded section 145 in opening 135.

FIG. 1C shows fastener 100 (as illustrated in isolation on FIG. 1A) received into opening 135 in bone specimen 120 (as illustrated in isolation on FIG. 1B). FIG. 1C shows threaded portion 102 on fastener 100 operably secured into threaded section 145 in opening 135. $D_F$ on fastener 100 is pre-selected to be no more than about 0.2 mm greater than $D_O$ at entry hole 140 in near cortex 125. The length of tapered portion 115 on fastener 100 (as shown on FIG. 1A) is pre-selected to enable fastener 100 (as shown in FIG. 1C) to contact entry hole 140 along the length of tapered portion 115 (shown on FIG. 1A). In this way, as fastener 100 on FIG. 1C is drawn into opening 135 by rotating threaded portion. 102 into threaded section 145, reference point 105 is moved closer to entry hole 140, urging $D_O$ on entry hole 140 to enlarge. Accordingly, radial preload is exerted at the interface of entry hole 140 and fastener 100, allowing the advantages of radial preload to benefit the securement of fastener 100 in bone specimen 120. However, in accordance with the invention, as fastener 100 is drawn further into opening 135, and as reference point 105 passes into entry hole 140, since $D_F$ is pre-selected to be no more than about 0.2 mm greater than $D_O$, the maximum amount of radial preload that securement of fastener 100 in bone specimen 120 can exert on entry hole 140 is about 0.2 mm. This value is consistent with the teaching of Biliouris et al., discussed in the background section of this disclosure, finding that about 0.2 mm is generally a maximum amount of radial preload that a specimen of cortical bone can withstand without suffering damage such as micro-cracking.

With further reference to FIGS. 1B and 1C, it will be appreciated that, although not illustrated, other embodiments may provide opening 135 with a profile through near cortex 125 that is shaped other than a cylindrical entry hole such as item 140, as illustrated. For example, the profile of opening 135 through near cortex 125 could be tapered. In such alternative embodiments, it will be understood that $D_O$, as illustrated on FIG. 1B, will be provided as a predetermined minimum entry diameter constricting the profile of opening 135 through near cortex 125.

Figure 2A:
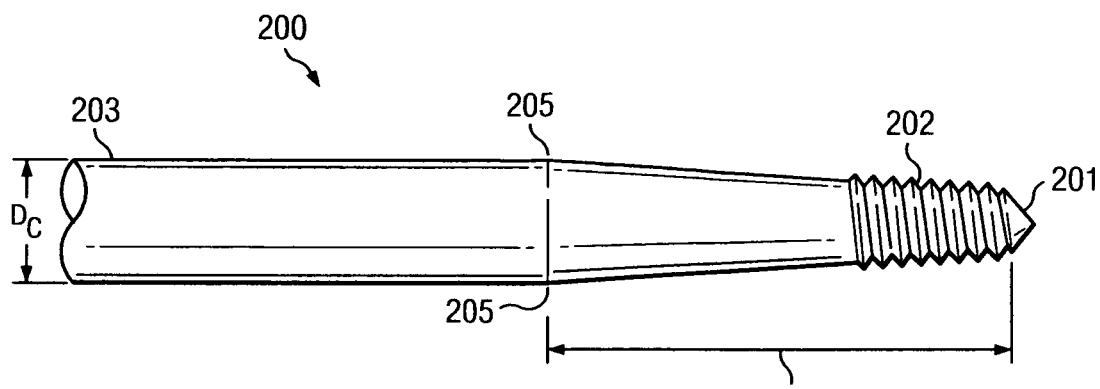
FIGS. 2A, 2B and 2C illustrate, according to a second aspect of the present disclosure, a deployment of fastener 200 into bone specimen 220 through opening 235.
Figure 2B:
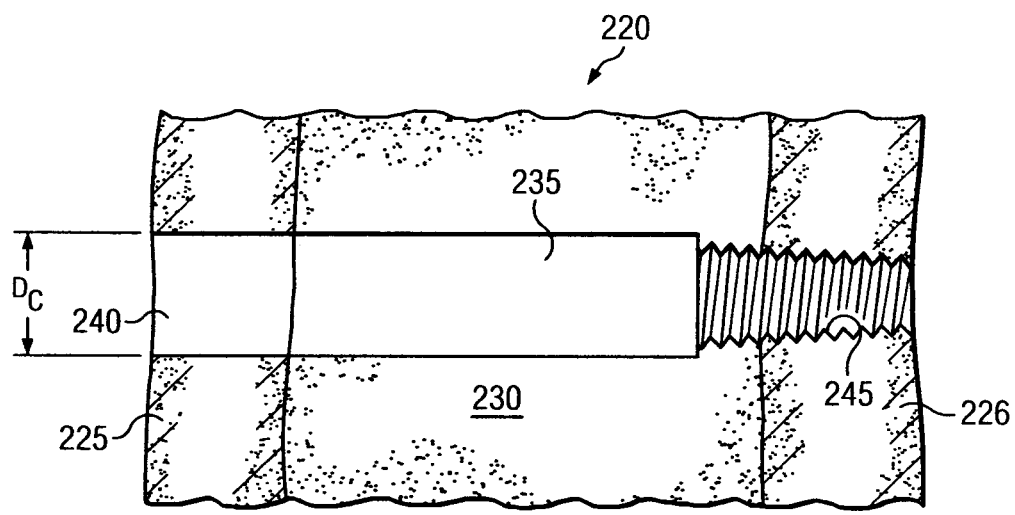
Figure 2C:
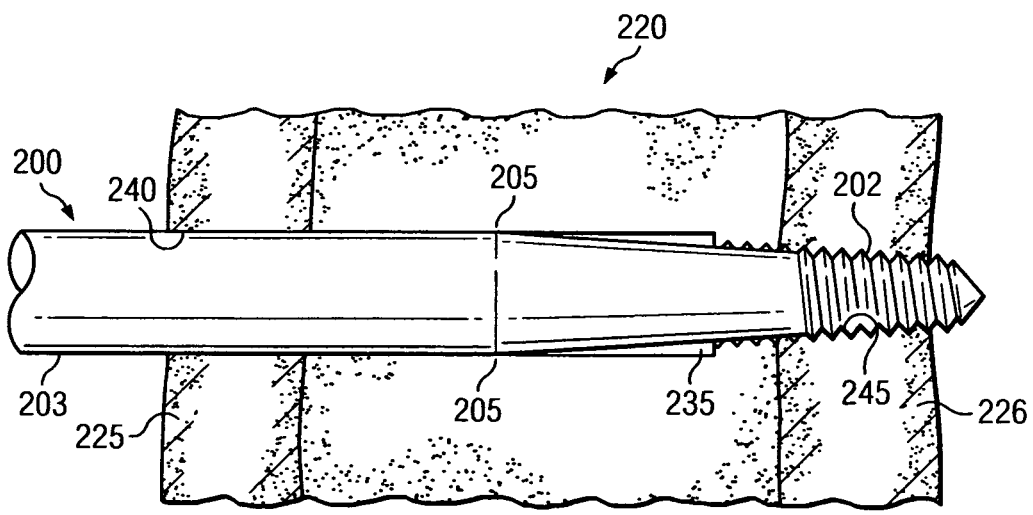

Turning now to FIGS. 2A, 2B and 2C, which should be viewed together, a second aspect of the present disclosure is illustrated, in which an orthopedic fastener 200 is configured to limit and/or control radial preloads exerted in far cortex 226 as fastener 200 is operably secured into bone specimen 220.

Referring first to FIG. 2A, orthopedic fastener 200 provides tapered portion 215 on one end 201 of fastener 200. Fastener 200 further provides unthreaded cylindrical portion 203 adjacent to tapered portion 215. Cylindrical portion. 203 is of constant diameter $D_C$. Reference point 205 on fastener 200 is the point at which tapered portion 215 and cylindrical portion 203 transition into one another. As shown on FIG. 2A, threaded portion 202 is deployed on tapered portion 215, at end 201 of fastener 200. FIG. 2A illustrates threaded portion 202 deployed only partially over tapered portion 215. It will be appreciated, however, in other embodiments (not illustrated), threaded portion 202 may deployed over the entire length of tapered portion 215.

The taper profile on tapered portion 215, whether constant or otherwise, is pre-selected. Moreover, as will be described in more detail further on, the dimensional characteristics of the threads on threaded portion 202 (such as diameter, pitch, depth and profile) are also pre-selected.

FIG. 2B illustrates bone specimen 220 in cross-section, showing near and far cortices 225, 226 surrounding interior portion 230. It will be appreciated that interior portion 230 may comprise cancellous bone and/or fatty bone marrow. Bone specimen 220 as illustrated on FIG. 2B has been prepared to receive fastener 200 from FIG. 2A. More specifically, opening 235 has been pre-configured to receive fastener 200. Circular entry hole 240 extends through near cortex 225 into interior portion 230 of bone specimen 220. In the embodiment illustrated in FIG. 2B, the diameter of entry hole 240 is pre-selected to be $D_C$, substantially the same diameter as the diameter of cylindrical portion 203 on fastener 200 (as shown on FIG. 2A). However, as will be discussed in more detail with reference to FIG. 2C, additional embodiments may provide entry hole 240 in bone specimen 220 with diameters or profiles other than $D_C$. The invention is not limited with respect to any particular diameter or profile of entry hole 240 in bone specimen 220.

With continuing reference to FIG. 2B, opening 235 further provides tapered female threaded section 245 provided in far cortex 226, wherein the threads on tapered female threaded section 245 are pre-selected to mate with threaded portion 202 on fastener 200 (as shown on FIG. 2A). In a preferred embodiment, such thread mating advantageously includes mating of thread taper, pitch, depth and profile.

FIG. 2C shows fastener 200 (as illustrated in isolation on FIG. 2A) received into opening 235 in bone specimen 220 (as illustrated in isolation on FIG. 2B). FIG. 2C shows threaded portion 202 on fastener 200 operably secured into threaded section 245 in opening 235. As noted immediately above in the discussion of FIG. 2B, the threads on threaded portion 202 on fastener 200 are pre-selected to mate with the threads on threaded section 245 in opening 235 in bone specimen 220. In this way, as fastener 200 on FIG. 2C is threadably engaged into opening 235, the taper on the interface between threaded portion 202 and threaded section 245 causes threads of increasingly larger diameter on threaded portion 202 to engage threaded section 245 in bone specimen 220. As a result, as fastener 200 on FIG. 2C is threadably engaged into opening 235, radial preload is imparted into the area of far cortex 226 immediately surrounding threaded section 245.

It will be appreciated that the inventive material disclosed herein is independent of the manufacturing method by which threaded section 245 is provided in opening 235. Threaded section 245 may be provided by any suitable technique, such as, without limitation, self-drilling, pre-drilling and reaming, or step-drilling, with subsequent tapping as required.

Since the thread characteristics of threaded portion 202 and threaded section 245 are pre-selected, a pre-desired amount of radial preload can be imparted into far cortex 226. Conventional methods may be used to measure, calculate or predict the amount of radial preload being imparted. For example, conventional algorithms or tables may be used to determine how many turns of fastener 200 will impart a pre-desired amount of radial preload. Alternatively, a conventional torque wrench may be used to tighten fastener 200, where pre-calibration (such as via a look-up table) will dictate how much torque imparted on fastener 200 is equivalent to a pre-determined desired amount of radial preload.

Figure 4A:
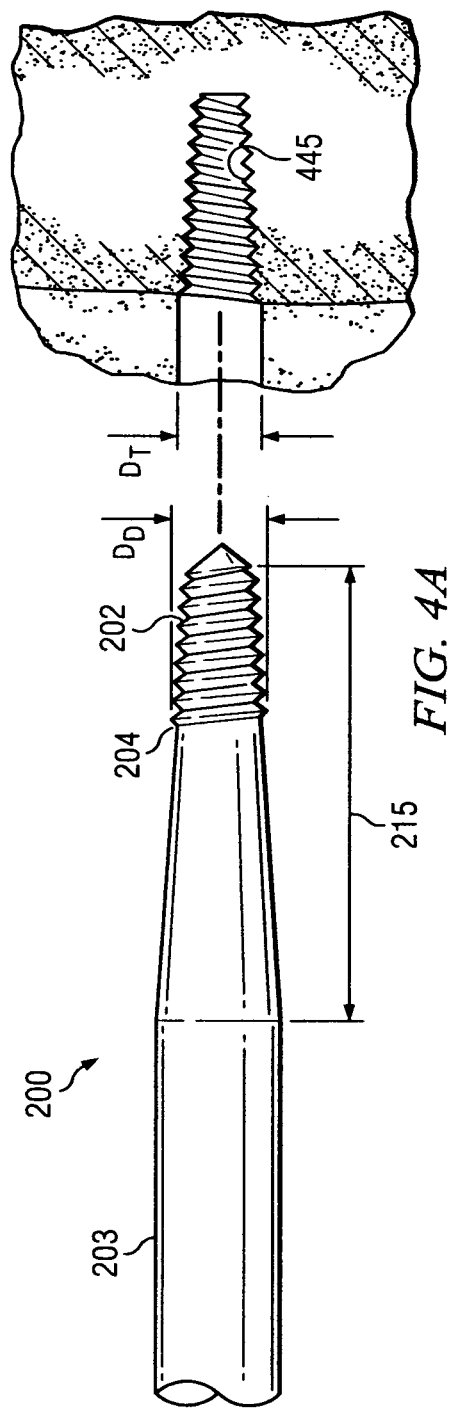
FIGS. 4A, 4B and 4C illustrate exemplary embodiments of structure that may be deployed on fasteners of the present invention to limit the maximum radial preload available to be imparted in "mating tapered thread" configurations described herein.
Figure 4B:
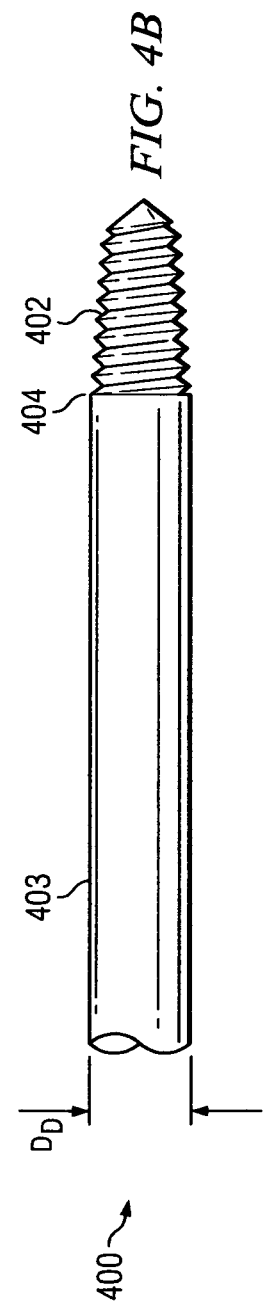
Figure 4C:
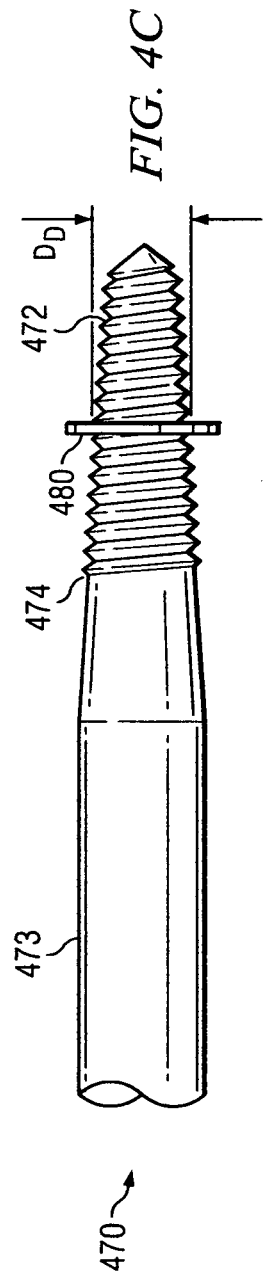

Alternatively, embodiments of fastener 200 may be provided to limit the maximum radial preload available to be imparted by further tightening fastener 200 once threaded portion 202 and threaded section 245 are threadably engaged. FIGS. 4A to 4C illustrate exemplary embodiments of structure configured to limit the maximum radial preload available to be imparted in such "mating tapered thread" configurations. It will be appreciated, however, that the inventive material disclosed herein is not limited to any particular structure provided to limit radial preload once threaded portion 202 and threaded section 245 are threadably engaged, if indeed any such structure to limit radial preload is provided at all.

FIG. 4A shows, as also illustrated on FIG. 2A, fastener 200 providing threaded portion 202 on tapered portion 215. In the embodiment illustrated in FIG. 4A, however, unthreaded portion 203 on fastener 200 is identified, as well as discontinuity 204. It will be appreciated that unthreaded portion 203 transitions into threaded portion 202 at discontinuity 204. FIG. 4A also identifies $D_D$ on fastener 200, the diameter along tapered portion 215 at which discontinuity 204 is provided.

FIG. 4A also shows tapered female threaded section 445 disposed to receive threaded portion 202 on fastener 200. It will be appreciated that in the embodiments for limiting "mating tapered thread" radial preload described with reference to FIGS. 4A to 4C, bone preparations such as threaded section 445 on FIG. 4A, disposed to receive threaded portion 202 on fastener 200, may be located in either near or far cortices of a bone specimen. The location of bone preparations such as threaded section 445 on FIG. 4A is independent of the inventive material disclosed herein describing structure configured to limit the maximum radial preload available to be imparted in "mating tapered thread" configurations.

Referring again to FIG. 4A, and analogous to threaded portion 202 and threaded section 245 as described above with reference to FIG. 2C, the threads on threaded portion 202 on FIG. 4A are pre-selected to mate with the threads on threaded section 445. Again analogous to threaded portion 202 and threaded section 245 on FIG. 2C, since the thread characteristics of threaded portion 202 on FIG. 4A and threaded section 445 are pre-selected, a pre-desired amount of radial preload can be imparted into the bone material surrounding threaded section 445 by threadably engaging threaded portion 202 on threaded section 445 and then further tightening. However, in the embodiment illustrated on FIG. 4A, threaded section 445 provides diameter $D_T$ at its widest opening (i.e., its entryway), and $D_D$ on fastener 200 and $D_T$ on threaded section 445 are pre-selected so that $D_D$ is no more than about 0.2 mm greater than $D_T$.

Now, with continued reference to FIG. 4A, it will be understood that as threaded portion 202 is threadably engaged on threaded section 445 and further tightened, discontinuity 204 on fastener 200 will act as a "stop" to prevent further tightening of fastener 200 into threaded section 445 once discontinuity 204 reaches the first thread on threaded section 445. Since $D_D$ on fastener 200 and $D_T$ on threaded section 445 are pre-selected so that $D_D$ is no more than about 0.2 mm greater than $D_T$, the maximum radial preload available to be imparted into the bone material surrounding threaded section 445 is no more than about 0.2 mm.

It will be readily appreciated that, within the scope of the embodiment illustrated in FIG. 4A, $D_D$ and $D_T$ can also be pre-selected to have different relative values, so as to limit the maximum radial preload available to be imparted to amounts other than about 0.2 mm. However, as taught by Biliouris et at, $D_D$ and $D_T$ in the embodiment illustrated in FIG. 4A should preferably be configured to limit the maximum radial preload available to about 0.2 mm in order to avoid cause micro-cracking and other damage to the cortical bone.

Further to FIG. 4A and the accompanying disclosure immediately above, FIG. 4B illustrates another embodiment of structure configured to limit the maximum radial preload available to be imparted in "mating tapered thread" configurations. Fastener 400 in FIG. 4B is similar to fastener 200 in FIGS. 2A and 4A, except that discontinuity 404 separates tapered threaded portion 402 and cylindrical unthreaded portion 403. Threaded portion 402 on fastener 400 on FIG. 4B is, however, inventively the same in all respects as threaded portion 202 on FIG. 4A, with $D_D$ identified as the diameter at discontinuity 404. In the embodiment of FIG. 4B, however, $D_D$ on threaded portion 402 is the same as the cylindrical diameter of unthreaded portion 403. It will be appreciated that in some applications, the embodiment illustrated in FIG. 4B may be more convenient to manufacture, by cutting threaded portion 402 onto a cylindrical profile with a pre-selected diameter of $D_D$. In such embodiments, it will be understood to be important to establish discontinuity 404 at the transition from unthreaded portion 403 to threaded portion 402 via, for example, a thread profile transition effective to prevent further tightening of fastener 400 once the thread(s) at $D_D$ on threaded portion 402 engage the thread(s) at $D_T$ on threaded section 445 (as illustrated on FIG. 4A).

Further to FIGS. 4A and 4B, and the corresponding accompanying disclosure immediately above, FIG. 4C illustrates yet another embodiment of structure configured to limit the maximum radial preload available to be imparted in "mating tapered thread" configurations. Fastener 470 in FIG. 4C is similar to fastener 200 in FIGS. 2A and 4A, except that discontinuity 474 separates tapered threaded portion 472 and tapered unthreaded portion 473 at a point of larger diameter than is desired to be pre-selected as $D_D$. Stop 480 is provided instead on threaded portion 472 at pre-selected diameter $D_D$. It will be appreciated that with the exception of stop 480, rather than discontinuity 474, being provided on threaded portion 472 to define $D_D$, threaded portion 472 on fastener 470 on FIG. 4C is, however, inventively the same in all respects as threaded portion 202 on FIG. 4A. In this way, if fastener 470 on FIG. 4C is threadably engaged on threaded section 445 on FIG. 4A and further tightened, stop 480 will prevent further tightening of fastener 470 into threaded section 445 once stop 480 reaches the first thread on threaded section 445.

Stop 480 on fastener 470 is illustrated on FIG. 4C as a washer. The inventive material disclosed herein is not limited in this regard, however. Stop 480 may be any structure on threaded portion 472 suitable to define $D_D$ and to prevent further tightening past $D_D$. Other examples might include a lip or the head of a screw or bolt.

With reference back now to FIG. 2C, it will be appreciated that when fastener 200 is threadably engaged into opening 235 so as to impart radial preload in far cortex 226, care should be taken so as not to exceed about 0.2 mm of radial preload. As taught by Biliouris et al., and discussed above, amounts of radial preload in excess of about 0.2 mm have been shown to cause micro-cracking and other damage to the cortical bone. Consideration should be given to deploying structure on fastener 200, such as, without limitation, structure from among the examples suggested above with reference to FIGS. 4A to 4C, in order to limit the maximum radial preload available to be imparted by "mating tapered thread" configurations to about 0.2 mm. It will be appreciated, however, that any such structure to limit radial preload imparted by mating tapered threads is optional within the scope of the inventive material disclosed herein.

As shown on FIGS. 2A and 2B, and discussed briefly above, the illustrated embodiment in FIGS. 2A, 2B and 2C provide cylindrical portion 203 on fastener 200 with substantially the same diameter $D_C$ as entry hole 240 on bone specimen 220. It will be readily appreciated, however, that in other embodiments (not illustrated) entry hole 240 may be provided with a diameter less than $D_C$. In this way, when fastener 200 is introduced into opening 235 on bone specimen 220, and cylindrical portion 203 is pressed into entry hole 240, radial preload may be imparted into near cortex 225.

Again, care should be exercised when providing an entry hole 240 on bone specimen 220 with diameter less than $D_C$, in order not to impart more than about 0.2 mm of radial preload when cylindrical portion 203 is pressed into entry hole 240. As taught by Biliouris et al., and as discussed above, radial preloads exceeding about 0.2 mm may damage near cortex 225. Indeed, it will be appreciated that further embodiments of fastener 200 (not illustrated) may provide an arrangement on near cortex 225 similar to those illustrated on FIG. 1C, in which a limited amount of radial preload is imparted when cylindrical portion 203 is pressed into a reduced-diameter entry hole 240. In these embodiments, tapered portion 215 (as shown on FIG. 2A) may be of a pre-selected length so that, when introduced into opening 235 on bone specimen 220 (as shown on FIG. 2C), reference points 205 are now located in near cortex bone 225, or outside of bone specimen 220 completely. The diameter of entry hole 240 in bone specimen 220 in these embodiments is pre-selected to be no smaller than about 0.2 mm less than $D_C$. By analogy to FIG. 1C and its accompanying disclosure above, such alternative (but not illustrated) embodiments will allow radial preload in near cortex 225 to be limited to no more than about 0.2 mm.

With further reference to FIGS. 2B and 2C, it will be appreciated that, although not illustrated, other embodiments may provide opening 235 with a profile through near cortex 225 that is shaped other than a cylindrical entry hole such as item 240, as illustrated. For example, the profile of opening 235 through near cortex 225 could be tapered. In such alternative embodiments, it will be understood that $D_C$, as illustrated on FIG. 2B, will be provided as a predetermined minimum entry diameter constricting the profile of opening 235 through near cortex 225.

Figure 3A:
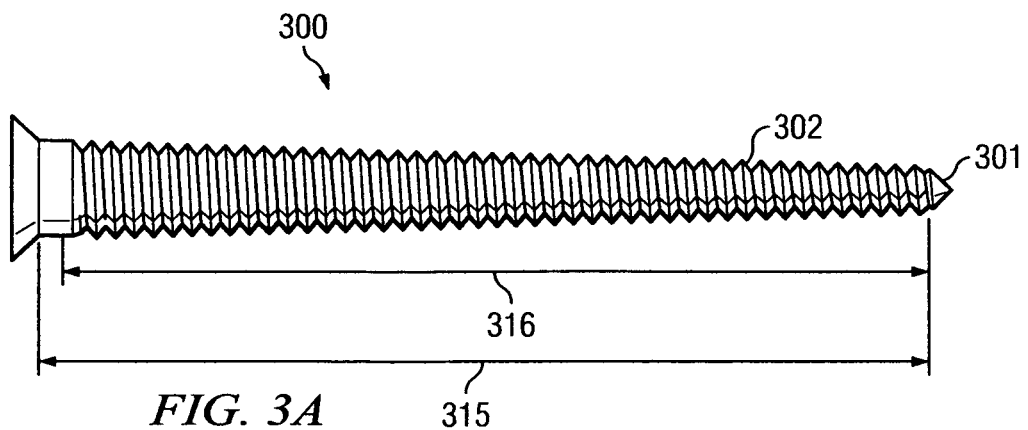
FIGS. 3A, 3B and 3C illustrate, according to a third aspect of the present disclosure, a deployment of fastener 300 into bone specimen 320 through opening 335.
Figure 3B:
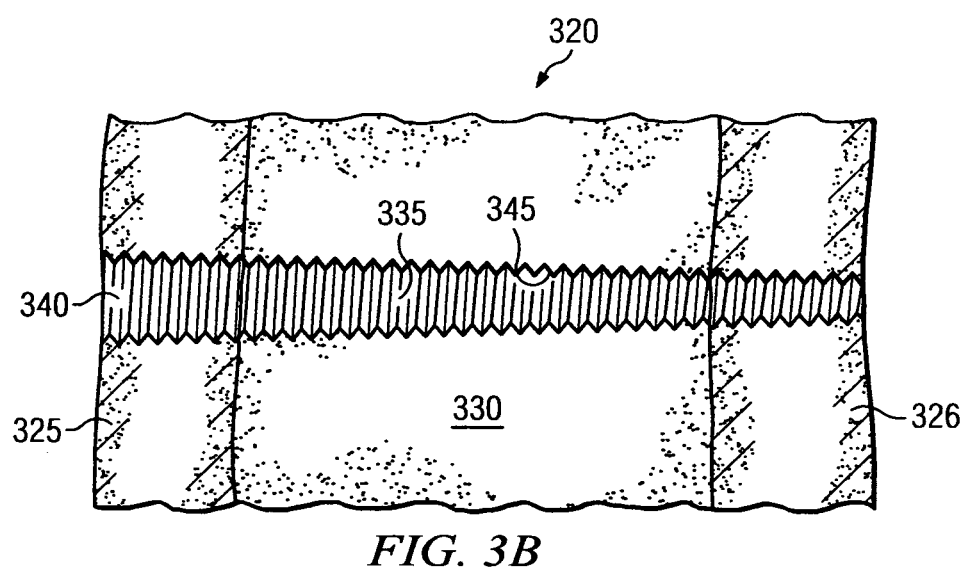
Figure 3C:
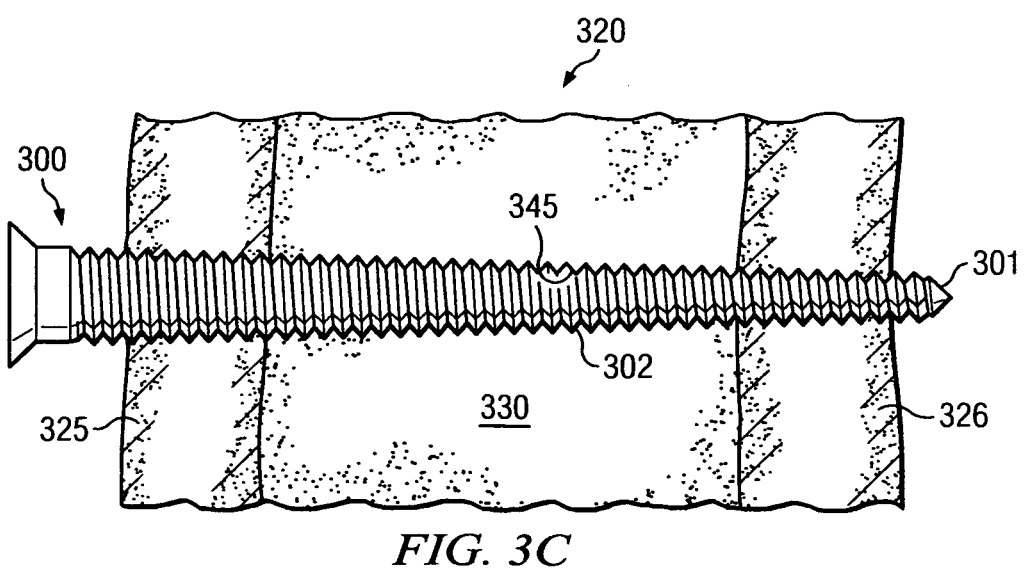

Turning now to FIGS. 3A, 3B and 3C, which should be viewed together, a third aspect of the present disclosure is illustrated, in which an orthopedic fastener 300 is configured to limit and/or control radial preloads exerted in both near cortex 325 and far cortex 326 as fastener 300 is operably secured into bone specimen 320. For general reference, subject to the detailed disclosure that follows, fastener 300, as shown operably secured in bone specimen 320 on FIG. 3C, limits and/or controls radial preloads in both near and far cortices 325 and 326 in functionally the same way as fastener 200 limits and/or controls radial preloads in far cortex 226 on FIG. 2C, as described above.

With reference first to FIG. 3A, orthopedic fastener 300 provides tapered portion 315 on one end 301 of fastener 300. Although the invention is not limited in this regard, FIG. 3A shows tapered portion 315 comprising substantially the entire length of fastener 300. Other embodiments (not illustrated) may provide fastener 300 with additional length via, for example, a cylindrical portion provided distal from end 301 and tapered portion 315, and/or a cylindrical portion appended to end 301.

FIG. 3A further illustrates threaded portion 302 provided on tapered portion 315, at end 301 of fastener 300. Threaded portion 302 is deployed over threaded portion length 316. FIG. 3A illustrates threaded portion length 316 deployed substantially over the entire length of tapered portion 315. It will be appreciated, however, in other embodiments (not illustrated, but discussed below with reference to FIG. 3C), threaded portion length 316 may be deployed at end 301 of fastener 300 but over only part of tapered portion 315.

The taper profile on tapered portion 315, whether constant or otherwise, is pre-selected. Further, threaded portion length 316 is also pre-selected. Moreover, as will be described in more detail further on, the dimensional characteristics of the threads on threaded portion 302 (such as diameter, pitch, depth and profile) are also pre-selected.

FIG. 3B illustrates bone specimen 320 in cross-section, showing near and far cortices 325, 326 surrounding interior portion 330. It will be appreciated that interior portion 330 may comprise cancellous bone and/or fatty bone marrow. Bone specimen 320 as illustrated on FIG. 3B has been prepared to receive fastener 300 from FIG. 3A. More specifically, opening 335 has been pre-configured to receive fastener 300. Opening 335 begins at entry 340, and provides tapered female threaded section 345 through near cortex 325, interior portion 330, and far cortex 326. The threads on tapered female threaded section 345 are pre-selected to mate with threaded portion 302 on fastener 300 (as shown on FIG. 3A). In a preferred embodiment, such thread mating advantageously includes mating of thread taper, pitch, depth and profile.

Analogous to the disclosure above describing FIGS. 2B and 2C, it will be appreciated on FIGS. 3B and 3C that the inventive material disclosed herein is independent of the manufacturing method by which female threaded section 345 is provided in bone specimen 320. Threaded section 345 may be provided by any suitable technique, such as, without limitation, self-drilling, pre-drilling and reaming, or step-drilling, with subsequent tapping as required.

FIG. 3C shows fastener 300 (as illustrated in isolation on FIG. 3A) received into opening 335 in bone specimen 320 (as illustrated in isolation on FIG. 3B). FIG. 3C shows threaded portion 302 on fastener 300 operably secured into threaded section 345 in opening 335. Note that notation of opening 335 has been omitted from FIG. 3C for clarity, but may be identified via reference to FIG. 3B.

It will be appreciated from FIG. 3C that threaded portion length 316 on fastener 300 (as shown on FIG. 3A) is pre-selected to enable threaded portion 302 on fastener 300 (as shown on FIG. 3C) to engage threaded section 345 on bone specimen 320 in both near cortex 325 and far cortex 326. Moreover, as noted immediately above in the discussion of FIG. 3B, the threads on threaded portion 302 on fastener 300 are pre-selected to mate with the threads on threaded section 345 in opening 335 in bone specimen 320. In this way, as fastener 300 on FIG. 3C is threadably engaged into opening 335, the taper on the interface between threaded portion 302 and threaded section 345 causes threads of increasingly larger diameter on threaded portion 302 to engage threaded section 345 in bone specimen 320.

As a result, as fastener 300 on FIG. 3C is threadably engaged into opening 335, radial preload is imparted into the areas of near cortex 325, interior portion 330 and far cortex 326 immediately surrounding threaded section 345. As noted above, this mechanism to impart radial preload is functionally the same as the manner in which fastener 200 limits and/or controls radial preloads in far cortex 226 on FIG. 2C. It will be understood, however, that although fastener 300 on FIG. 3C is capable of imparting radial preload into interior portion 330 as well as near and far cortices 325 and 326, any radial preload operably retained in interior portion 330 is not of inventive significance to this disclosure. While such radial preload retained in interior portion 330, if any, may be of some practical assistance preventing loosening of fastener 300 under operating loads, the inventive focus of this disclosure is on radial preload imparted by fastener 300 on near and far cortices 325 and 326.

With further reference to FIG. 3C, since the thread characteristics of threaded portion 302 and threaded section 345 are pre-selected, a pre-desired amount of radial preload can be imparted into near cortex 325 and far cortex 326. Conventional methods may be used to measure, calculate or predict the amount of radial preload being imparted. For example, conventional algorithms or tables may be used to determine how many turns of fastener 300 will impart a pre-desired amount of radial preload. Alternatively, a conventional torque wrench may be used to tighten fastener 300, where pre-calibration (such as via a look-up table) will dictate how much torque imparted on fastener 300 is equivalent to a pre-determined desired amount of radial preload.

It will be recalled from earlier disclosure herein that FIGS. 4A to 4C illustrate exemplary embodiments of structure configured to limit the maximum radial preload available to be imparted in "mating tapered thread" configurations, such as have just been described with reference to FIGS. 3A to 3C. It will be understood that any of the embodiments illustrated, disclosed or suggested above with respect to FIGS. 4A to 4C may be deployed on fastener 300 as illustrated and described with reference to FIGS. 3A to 3C. It will be further understood that any of the embodiments illustrated, disclosed or suggested above with respect to FIGS. 4A to 4C may be deployed on fastener 300 so as to limit the maximum radial preload available to be imparted in the near cortex only, in the far cortex only, or concurrently in both cortices. It will also be appreciated, however, that the inventive material disclosed herein is not limited to any particular structure provided to limit the maximum radial preload available to be imparted by fastener 300, if indeed any such structure to limit radial preload is provided at all in either cortex.

With reference back now to FIG. 3C, it will be appreciated that when fastener 300 is threadably engaged into opening 335 so as to impart radial preload in near cortex 325 and far cortex 326, care should be taken so as not to exceed about 0.2 mm of radial preload. As taught by Biliouris et al., and discussed above, amounts of radial preload in excess of about 0.2 mm have been shown to cause micro-cracking and other damage to the cortical bone. Consideration should be given to deploying structure on fastener 300, such as, without limitation, structure from among the examples suggested above with reference to FIGS. 4A to 4C, in order to limit the maximum radial preload available to be imparted by "mating tapered thread" configurations to about 0.2 mm. As noted above, however, it will be appreciated that any such structure to limit radial preload imparted by mating tapered threads is optional within the scope of the inventive material disclosed herein It was mentioned above in reference to FIG. 3A that, although not illustrated, additional length could be provided to fastener 300 via, for example, a cylindrical portion provided distal from end 301 and/or a cylindrical portion appended to end 301. With reference now to FIG. 3C, it will be appreciated that such additional length is not of inventive significance to this disclosure. Additional length, distal from end 301 and threaded portion length 316, may be provided to fastener 300 by any structural means, so long as threaded portion length 316 (as shown on FIG. 3A) is pre-selected to permit threaded portion 302 on fastener 300 (as shown on FIG. 3C) to engage threaded section 345 in both near cortex 325 and far cortex 326.

Throughout this disclosure so far, embodiments of fasteners have been described with structural features that may be pre-selected to match corresponding features of bone openings into which they may be received. It will be further appreciated, however, that the converse is true without departing from the spirit and scope of the inventive material disclosed herein. More specifically, with particular reference to FIGS. 1C, 2C and 3C, it will be appreciated that fasteners according to this disclosure may be manufactured as "rated" to be received in corresponding bone hole preparations. It will be understood that when a fastener is rated to be received in a corresponding bone hole preparation, the fastener is manufactured with accompanying disclosure from the manufacturer regarding specific characteristics of a corresponding bone hole preparation that will engage the inventive functionality of the fastener.

For example, in the embodiments disclosed in FIGS. 1A, 1B and 1C, fastener 100 may be manufactured as rated to be received in a corresponding bone hole preparation comprising: (1) a diameter $D_O$ of entry hole 140 that is pre-selected to be smaller than $D_F$ of cylindrical portion 103 on fastener 100, but no more than about 0.2 mm smaller than $D_F$; and (2) an overall thickness of bone specimen 120 that is pre-selected to be in a range of thicknesses that permit tapered portion 115 on fastener 100 to contact entry hole 140 when threaded portion 102 is threadably engaged in far cortex 126.

Similarly, by way of further example in the embodiments disclosed in FIGS. 2A, 2B and 2C, fastener 200 may be manufactured as rated to be received in a corresponding bone hole preparation comprising: (1) a diameter $D_C$ of entry hole 240 that is pre-selected to be substantially the same as $D_C$, the diameter of cylindrical portion 203 on fastener 200, but in no circumstances more than about 0.2 mm smaller than $D_C$; and (2) a threaded section 245 provided in far cortex 226 that is pre-selected to mate with threaded portion 202 on fastener 200 for taper, thread pitch, thread depth and thread profile.

Similarly, by way of further example in the embodiments disclosed n FIGS. 3A, 3B and 3C, fastener 300 may be manufactured as rated to be received in a corresponding bone hole preparation comprising: (1) a threaded section 345 provided in near cortex 325 through to far cortex 326 that is pre-selected to mate with threaded portion 302 on fastener 300 for taper, thread pitch, thread depth and thread profile; and (2) an overall thickness of bone specimen 320 that is pre-selected to be in a range of thicknesses that permit threaded portion length 316 on fastener 300 to engage threaded section 345 in both near cortex 325 and far cortex 326.

Embodiments of the invention have been described herein with reference to orthopedic fixation pins. It will be appreciated, however, that the invention is not limited in this regard, and that it may be embodied on any orthopedic fastener, such as, without limitation, pedicle screws, orthopedic nails, bone screws, hip screws, or even dental implants.

Those of ordinary skill in this art will further appreciate that the invention is not limited to any particular size of orthopedic fastener.

Although the present invention and its advantages have been described in detail, it should be understood that various changes, substitutions and alternations can be made herein without departing from the spirit and scope of the invention as defined by the appended claims.

I claim:

1. A method for limiting radial preload in securing an orthopedic fastener into a corresponding bone specimen, the method comprising the steps of:

(A) selecting the corresponding bone specimen to have an overall outer thickness from near cortex to far cortex in a predetermined range of outer bone thicknesses; and
(B) securing a fastener into the bone specimen, the fastener comprising means for imparting radial preload into the near cortex as the fastener is operably secured into the far cortex through an opening in the near cortex, the fastener further comprising means for limiting said radial preload to a maximum of about 0.2 mm.

2. The method of claim 1, in which the fastener further comprises means for imparting radial preload into the far cortex as the fastener is operably secured into the far cortex through an opening in the near cortex, and in which the means for imparting radial preload into the far cortex comprises a plurality of tapered male threads having a pre-selected thread profile.

3. The method of claim 2, in which the fastener further comprises means for limiting the maximum radial preload available to be imparted into the far cortex.

4. The orthopedic fastener of claim 2, further comprising means for limiting the maximum radial preload available to be imparted into the far cortex to about 0.2mm.

5. A method for limiting radial preload in securing an orthopedic fastener into a corresponding bone specimen, the method comprising the steps of:
(A) selecting and preparing the corresponding bone specimen to have (1) an overall outer thickness from near cortex to far cortex in a predetermined range of outer bone thicknesses, and (2) a predetermined bone hole preparation including an entry portion in the near cortex, the entry portion having a predetermined minimum entry diameter;
(B) providing a fastener, the fastener including a shank having adjacent threaded and unthreaded portions, the unthreaded portion providing a tapered diameter portion located at a preselected location on the shank, the tapered diameter portion transitioning from a large taper diameter to a small taper diameter, the small taper diameter located proximate to the threaded portion, the large taper diameter located distal from the threaded portion, the small taper diameter not greater than the predetermined minimum entry diameter in the bone hole preparation, the large taper diameter not greater than about 0.2 mm more than said predetermined minimum entry diameter; and
(C) limiting radial preload in the near cortex to not more than about 0.2 mm by securing the threaded portion on the fastener into the far cortex of the bone specimen so that the tapered diameter portion of the fastener contacts the entry portion in the near cortex.

6. The method of claim 5, in which step (A) includes preparing the bone specimen to further comprise an entry portion in the near cortex including a cylindrical entry hole of predetermined hole diameter, and in which (1) the small taper diameter on the fastener is not greater than said predetermined hole diameter, and (2) the large taper diameter on the fastener is not greater than about 0.2 mm more than said predetermined hole diameter.

7. The method of claim 5, in which step (A) includes preparing the bone specimen to further comprise a female threaded section provided in the far cortex, threads on the female threaded section configured to threadably engage with threads on the threaded portion of the fastener.

8. The method of claim 5, in which the threaded portion on the fastener includes self-tapping threads suitable for anchoring into cortical bone.

9. The method of claim 5, in which step (A) includes preparing the bone specimen to further include a tapered female threaded section in the far cortex, threads on the tapered female threaded section having a pre-selected thread profile, and in which the threaded portion on the fastener further comprises:
a plurality of male tapered threads, the male tapered threads configured to mate, according to the pre-selected thread profile, with corresponding threads on the tapered female threaded section;
the pre-selected thread profile having a predetermined thread geometry, said thread geometry predetermined so that, when the male tapered threads on the fastener are fully engaged in the tapered female threaded section on the bone hole preparation, a predetermined further tightening of the fastener imparts a corresponding predetermined radial preload on bone tissue surrounding the tapered female threaded section.

10. The method of claim 9, in which:
the plurality of male tapered threads includes a thread stop, the thread stop located such that the thread stop enables no more than a maximum male thread diameter $D_D$ on the plurality of male tapered threads to engage the tapered female threaded section in the far cortex;
the tapered female threaded section provides a maximum female thread diameter $D_T$; and
$D_D$ and $D_T$ are pre-selected so that $(D_D-D_T)$ provides a maximum radial preload available to be imparted on bone tissue surrounding the tapered female threaded section.

11. The method of claim 10, in which $D_D$ and $D_T$ are pre-selected so that $(D_D-D_T)$ is about 0.2 mm.

12. The orthopedic fastener of claim 10, in which the thread stop is selected from the group consisting of:
(a) a thread discontinuity;
(b) a washer;
(c) a lip; and
(d) a fastener head.

13. A method for limiting radial preload in securing an orthopedic fastener into a corresponding bone specimen, the method comprising the steps of:
(A) selecting and preparing the corresponding bone specimen to have (1) an overall outer thickness from near cortex to far cortex in a predetermined range of outer bone thicknesses, and (2) a predetermined bone hole preparation including a cylindrical entry hole in the near cortex of predetermined entry hole diameter;
(B) providing a fastener, the fastener including a shank having adjacent threaded and unthreaded portions, the unthreaded portion providing a tapered diameter portion located at a preselected location on the shank, the tapered diameter portion transitioning from a large taper diameter to a small taper diameter, the small taper diameter located proximate to the threaded portion, the large taper diameter located distal from the threaded portion, the small taper diameter not greater than the predetermined entry hole diameter in the bone hole preparation, the large taper diameter not greater than about 0.2 mm more than the predetermined entry hole diameter; and
(C) limiting radial preload in the near cortex to not more than about 0.2 mm by securing the fastener into the far cortex of the bone specimen so that the tapered diameter portion of the fastener contacts the cylindrical entry hole in the near cortex.

14. The method of claim 13, in which step (A) includes preparing the bone specimen to further comprise a female threaded section provided in the far cortex, threads on the female threaded section configured to threadably engage with threads on the threaded portion of the fastener.

15. The method of claim 13, in which the threaded portion on the fastener includes self-tapping threads suitable for anchoring into cortical bone.

16. The method of claim 13, in which step (A) includes preparing the bone specimen to further include a tapered female threaded section in the far cortex, threads on the tapered female threaded section having a pre-selected thread profile, and in which the threaded portion on the fastener further comprises:
  a plurality of male tapered threads, the male tapered threads configured to mate, according to the pre-selected thread profile, with corresponding threads on the tapered female threaded section;
  the pre-selected thread profile having a predetermined thread geometry, said thread geometry predetermined so that, when the male tapered threads on the fastener are fully engaged in the tapered female threaded section on the bone hole preparation, a predetermined further tightening of the fastener imparts a corresponding predetermined radial preload on bone tissue surrounding the tapered female threaded section.

17. The method of claim 16, in which:
  the plurality of male tapered threads includes a thread stop, the thread stop located such that the thread stop enables no more than a maximum male thread diameter $D_D$ on the plurality of male tapered threads to engage the tapered female threaded section in the far cortex;
  the tapered female threaded section provides a maximum female thread diameter $D_T$; and
  $D_D$ and $D_T$ are pre-selected so that $(D_D\text{-}D_T)$ provides a maximum radial preload available to be imparted on bone tissue surrounding the tapered female threaded section.

18. The method of claim 17, in which $D_D$ and $D_T$ are pre-selected so that $(D_D\text{-}D_T)$ is about 0.2 mm.

19. The orthopedic fastener of claim 17, in which the thread stop is selected from the group consisting of:
  (a) a thread discontinuity;
  (b) a washer;
  (c) a lip; and
  (d) a fastener head.

* * * * *